United States Patent
Munier et al.

(10) Patent No.: US 12,276,763 B2
(45) Date of Patent: Apr. 15, 2025

(54) METHOD FOR PROCESSING DATA RELATING TO A RADIOLOGICAL EXAMINATION OF A PATIENT

(71) Applicants: Fibermetrix, Entzheim (FR); Alara Expertise, Entzheim (FR)

(72) Inventors: Mélodie Munier, Ostwald (FR); Fanny Carbillet, Ostwald (FR); Pierre-Benoît Prudhomme, Strasbourg (FR); Nicolas Guillochon, Belfort (FR)

(73) Assignees: Fibermetrix, Entzheim (FR); Alara Expertise, Entzheim (FR)

( * ) Notice: Subject to any disclaimer, the term of this patent is extended or adjusted under 35 U.S.C. 154(b) by 187 days.

(21) Appl. No.: 17/999,491

(22) PCT Filed: Mar. 31, 2021

(86) PCT No.: PCT/FR2021/050562
§ 371 (c)(1),
(2) Date: Nov. 21, 2022

(87) PCT Pub. No.: WO2021/234234
PCT Pub. Date: Nov. 25, 2021

(65) Prior Publication Data
US 2023/0211181 A1    Jul. 6, 2023

(30) Foreign Application Priority Data
May 21, 2020  (FR) ..................................... 2005393

(51) Int. Cl.
G01T 1/02 (2006.01)
A61B 6/00 (2006.01)
(Continued)

(52) U.S. Cl.
CPC .............. G01T 1/023 (2013.01); A61B 6/032 (2013.01); A61B 6/5294 (2013.01); A61B 6/582 (2013.01); G01T 1/201 (2013.01); G16H 30/20 (2018.01)

(58) Field of Classification Search
None
See application file for complete search history.

(56) References Cited

U.S. PATENT DOCUMENTS

| 5,704,890 A | 1/1998 | Bliss et al. |
| 7,082,183 B2 * | 7/2006 | Toth ........................ A61B 6/032 378/4 |

(Continued)

FOREIGN PATENT DOCUMENTS

| FR | 3053799 B1 | 8/2022 |
| JP | 2020171458 A * | 10/2020 |

(Continued)

OTHER PUBLICATIONS

International Search Report for International Application No. PCT/FR2021/050562 Dated Jun. 30, 2022, 2 pages.

(Continued)

Primary Examiner — Thomas R Artman
(74) Attorney, Agent, or Firm — TraskBritt

(57) ABSTRACT

A method for processing data relating to a radiological examination of a patient by way of a determining device, comprises the steps of acquiring doses (Ci, ti) measured at a plurality of times ti, storing these time-stamped measurements of radiation doses, and acquiring at least one DICOM digital file containing information on the examination, wherein the method comprises the following steps: acquiring and storing at least one DICOM digital file delivered by the tomograph during or after a tomography; acquiring and storing time-stamped measurements of the doses detected via a scintillating fiber placed on the table, and time-stamped (Continued)

movements of the table; interpolating the measurements ($C_i$, $t_i$) with data of the image (DICOM) in a common interpolated space and constructing a table ($C_k$, DICOMk) in the interpolated space; and determining a table of the average dose levels $T_z$ in each slice T depending on the data (DICOMk, $C_k$).

6 Claims, 3 Drawing Sheets

(51) Int. Cl.
  *A61B 6/03* (2006.01)
  *A61B 6/58* (2024.01)
  *G01T 1/20* (2006.01)
  *G16H 30/20* (2018.01)

(56) References Cited

U.S. PATENT DOCUMENTS

| | | |
|---|---|---|
| 7,627,079 B2 | 12/2009 | Boone |
| 8,189,740 B2 | 5/2012 | Tsukagoshi et al. |
| 8,714,818 B2 | 5/2014 | Tesic et al. |
| 9,649,079 B1 * | 5/2017 | Guntzer ................ G06T 7/0012 |
| 10,507,003 B2 * | 12/2019 | Uber, III ................ A61B 6/488 |
| 10,838,077 B2 * | 11/2020 | Munier ................... G01T 1/20 |
| 10,962,656 B2 * | 3/2021 | Munier ................... G01T 1/023 |
| 11,246,558 B2 * | 2/2022 | Uber, III ............. A61B 6/4417 |
| 11,278,252 B2 * | 3/2022 | Notohara ................ G01T 1/02 |
| 2006/0018435 A1 | 1/2006 | Toth et al. |
| 2006/0027756 A1 | 2/2006 | Thomson et al. |
| 2008/0292055 A1 * | 11/2008 | Boone ................... G01T 1/2985 378/97 |
| 2009/0074143 A1 * | 3/2009 | Tsukagoshi ............ A61B 6/542 378/97 |
| 2012/0150505 A1 * | 6/2012 | Couch ...................... G01T 1/02 703/2 |
| 2012/0294419 A1 * | 11/2012 | Tesic .................... G01N 23/046 250/369 |
| 2018/0242944 A1 * | 8/2018 | Uber, III ................ A61B 6/037 |
| 2019/0310381 A1 * | 10/2019 | Munier ................... G01T 1/023 |
| 2020/0025946 A1 * | 1/2020 | Munier ................... G01T 1/023 |
| 2020/0146647 A1 * | 5/2020 | Uber, III ................ A61B 8/587 |
| 2020/0214657 A1 * | 7/2020 | Notohara ................. G01T 1/02 |
| 2023/0211181 A1 * | 7/2023 | Munier ................... G01T 1/201 378/65 |

FOREIGN PATENT DOCUMENTS

| | | | | |
|---|---|---|---|---|
| KR | 10-2015-0061520 A | | 6/2015 | |
| WO | 2012/129661 A1 | | 10/2012 | |
| WO | WO-2018007763 A1 | * | 1/2018 | ............ G01T 1/023 |
| WO | 2019/064652 A1 | | 4/2019 | |

OTHER PUBLICATIONS

International Written Opinion for International Application No. PCT/FR2021/050562 dated Jun. 30, 2022, 5 pages.

* cited by examiner

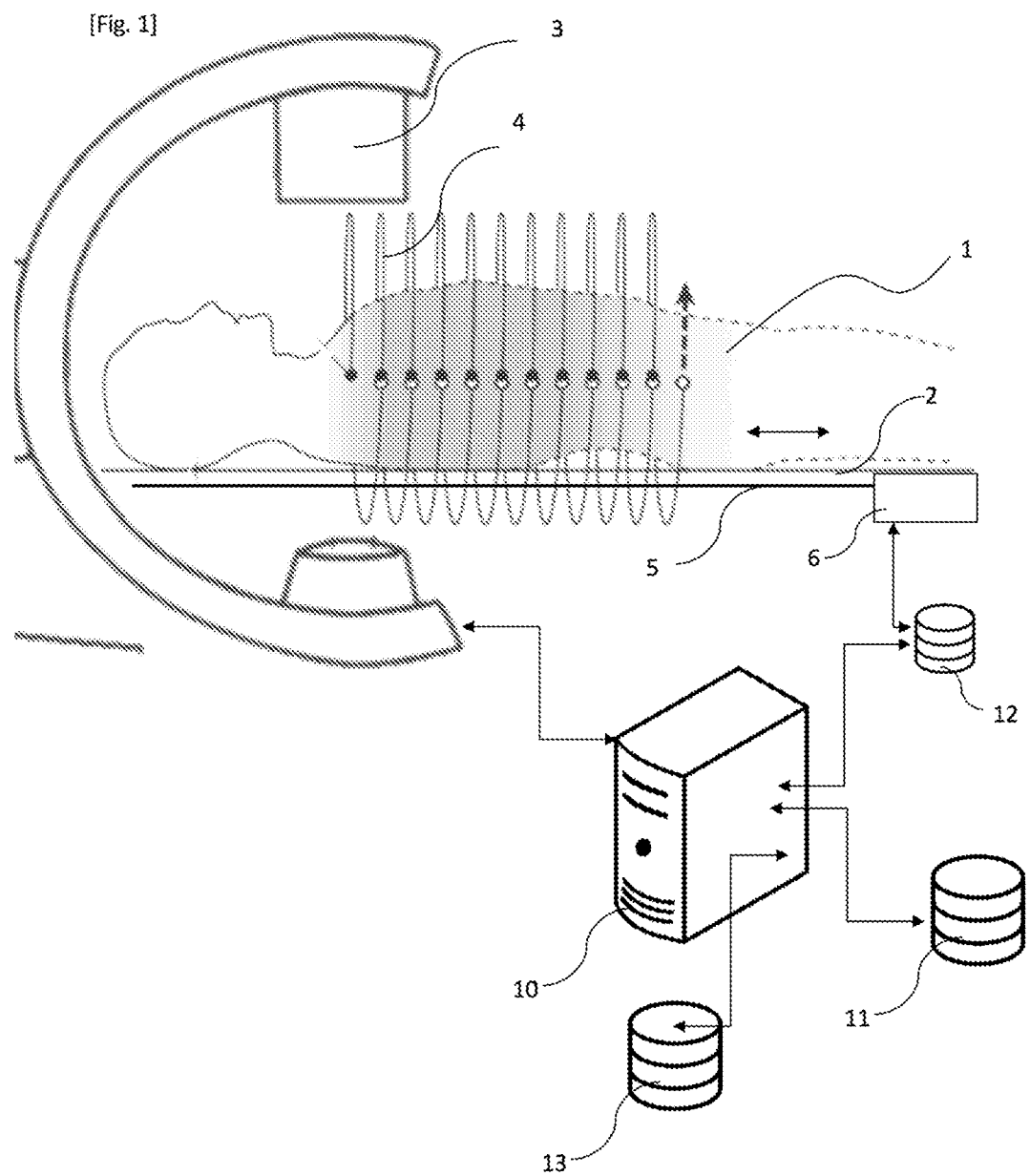
[Fig. 1]

[Fig. 2]
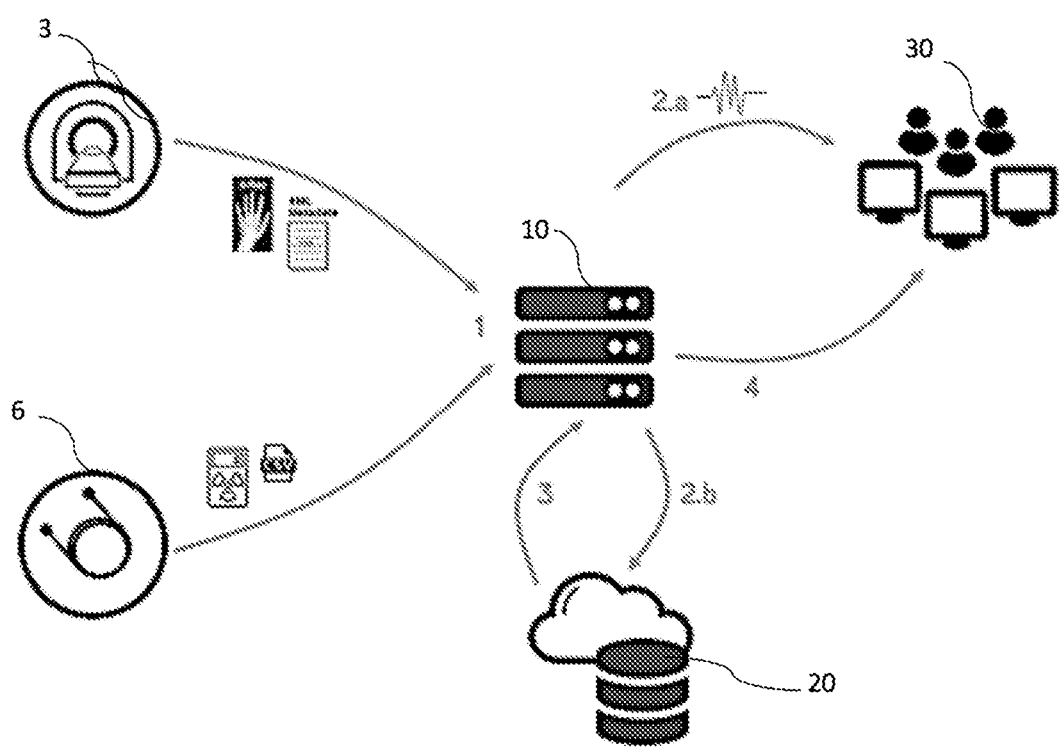

[Fig. 3]
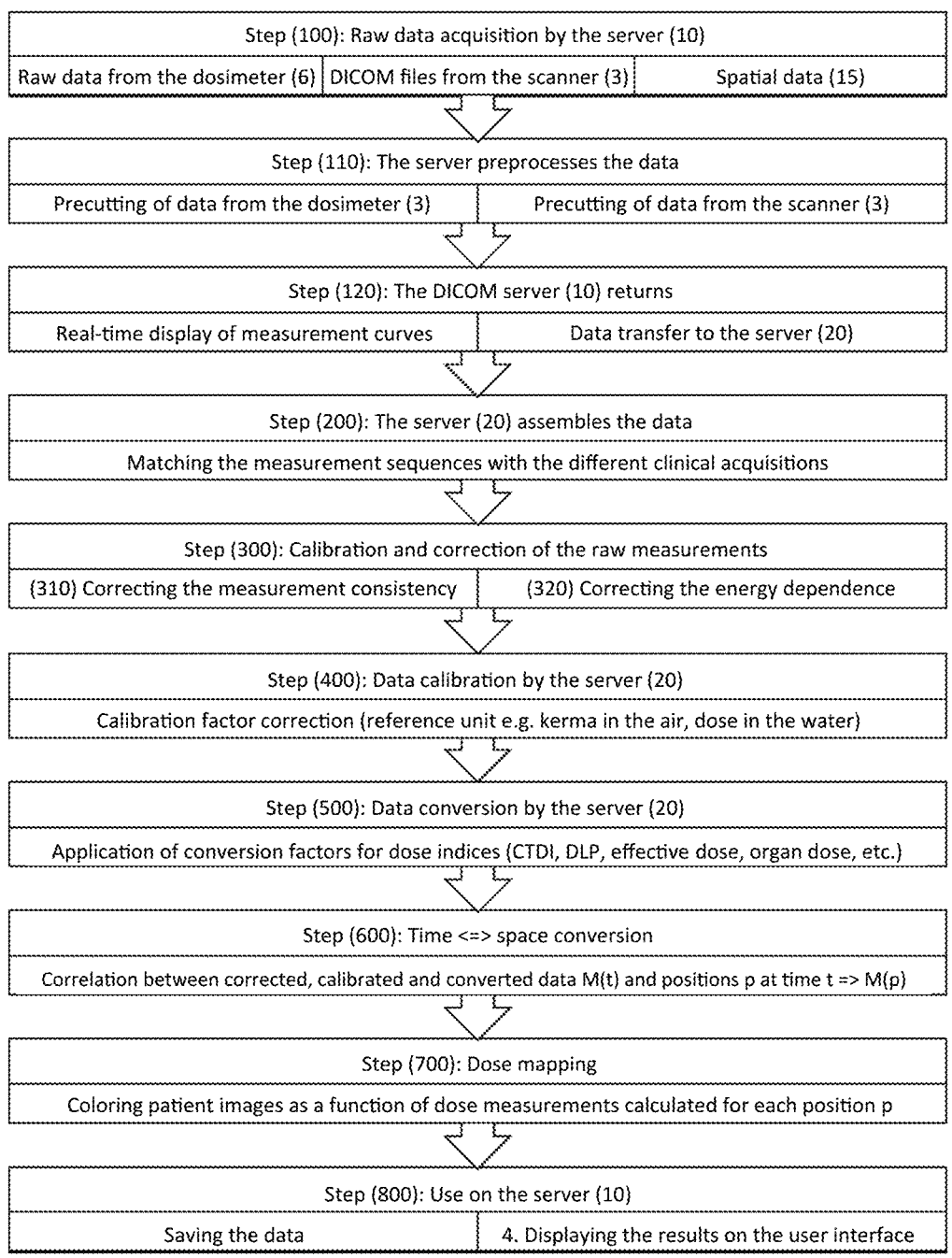

METHOD FOR PROCESSING DATA RELATING TO A RADIOLOGICAL EXAMINATION OF A PATIENT

CROSS-REFERENCE TO RELATED APPLICATIONS

This application is a national phase entry under 35 U.S.C. § 371 of International Patent Application PCT/FR2021/050562, filed Mar. 31, 2021, designating the United States of America and published as International Patent Publication WO 2021/234234 A1 on Nov. 25, 2021, which claims the benefit under Article 8 of the Patent Cooperation Treaty to French Patent Application Serial No. 2005393, filed May 21, 2020.

TECHNICAL FIELD

The present disclosure relates to the field of computed tomography (CT), and more particularly to the field of characterizing radiation doses received by patients during CT imaging examinations.

BACKGROUND

Current scanners measure the intensity of the rays delivered by the X-ray tube after they have been partially absorbed during their passage through the body, using a rotating frame carrying a source driven in rotation around the patient, or using a frame bearing immobile receptors forming a complete ring.

The data obtained is then processed by computer, which makes it possible to recompose two-dimensional sectional views and then three-dimensional views of the organs. It is possible to bring out the contrast of certain tissues, in particular, blood vessels, by injecting a so-called "contrast" product (an iodine complex) that has the property of strongly absorbing X-rays and therefore making the tissues where this product is present highly visible (which then appear hyperdense, that is to say, more "white," on the image). Owing to multi-detector (or multi-array) CT scanners with spiral acquisition (slow movement of the examination table during acquisition), since the 1990s we have obtained a very precise exploration of a large volume of the human body for an acquisition time of a few seconds.

A CT scanner can produce over 1,000 images of a patient's body part to be scanned, usually the head, chest, abdomen or pelvis. As with any X-ray, repeated exposure to X-rays can be harmful to the body, but the benefit/risk ratio associated with irradiation is largely in favor of computed tomography when the request for examination is justified, which makes it an increasingly popular medical imaging technique. Magnetic resonance imaging (MRI), a non-irradiating technique using magnetic fields, represents an alternative or a complement for certain applications, but cannot replace CT imaging in all indications.

Due to the medical value of this type of examination, computed tomography has become the largest contributor to the radiation dose in the population. The radiation dose associated with computed tomography has always been a concern, but the increased use of computed tomography in a wide range of diagnostic situations coupled with the high output capabilities of modern CT scanners heightens these concerns. It becomes necessary to know the precise quantity of radiation actually emitted and therefore the dose actually received by the patient and to evaluate the value of the radiological procedure, i.e., to justify the act with regard to alternative techniques giving rise to less or even no irradiation and, if necessary, to do everything possible to minimize and streamline the dose delivered to the patient.

PRIOR ART

In order to provide the operator with relevant information concerning the radiation dose to which a patient has been subjected during computed tomography (CT), a method has been proposed in U.S. Pat. No. 7,627,079B2 consisting of:

Subjecting a patient to an X-ray beam from an X-ray source;

Determining a primary X-ray radiation dose from the X-ray beam; and

Determining a scattered X-ray radiation dose from the X-ray beam.

Determining the primary radiological radiation dose comprises calculating a primary dose distribution from CT image data generated during scanning of the patient and calculating a radiation dose delivered to the patient based on the primary X-ray radiation dose and the scattered X-ray radiation dose.

The properties used to calculate the primary dose distribution comprise an X-ray source mA modulation scheme used to calculate the radiation dose delivered to the patient.

This prior art method uses the digital tomography image dataset generated during the patient scan as input, and one or more parameters related to an X-ray source are used to calculate the radiation dose delivered to the patient based on the image dataset and the X-ray source parameter(s).

The radiation dose is found by calculating a primary X-ray dose distribution and a scattered X-ray dose distribution from the CT image dataset and taking the sum of the primary X-ray dose distribution and the scattered X-ray dose distribution.

This solution is not satisfactory because it provides an exposure indicator determined from a more or less relevant theoretical model and not from the reality of the radiation to which the patient has been subjected.

Korean patent application KR20150061520A describes another example of a radiation dose assessment method so that a user can easily calculate the amount of radiation received by the patient during an imaging session in a tomographic scanner. This solution is also based on an estimate of the dose to which the patient is exposed.

Also known is U.S. Pat. No. 7,627,079B2, which relates to calculating the radiation dose delivered to a patient during computed tomography. The computed tomography image dataset generated during the patient scan and one or more parameters relating to an X-ray source are used to calculate the radiation dose delivered to the patient as a function of the dataset and the additional parameter(s) of the source. The radiation dose is generally found by calculating a distribution of a primary X-ray dose and a distribution of a scattered X-ray dose from the dataset and taking the sum of the distributions.

This solution is also an indirect estimation of the dose delivered to the patient.

U.S. Pat. No. 8,189,740 discloses an X-ray computed tomography apparatus, a scan plane assistance apparatus and a method for scan plane assistance that improves operator awareness of the radiation exposure dose.

The X-ray CT apparatus that transmits X-rays to a subject based on a set scan condition and reconstructs images from detected X-rays that pass through the subject, including a scan plane setting unit configured to set the scan condition, a reference dose storage unit configured to store reference dose information including a relationship between attribute information on a plurality of subject types and the corresponding reference dose and an exposure dose calculation unit configured to calculate an exposure dose corresponding to the set scan condition in accordance with the timing of setting the scan condition.

Patent FR3053799 by the applicant is also known, describing a device for the real-time determination of the dose deposited during a radiological examination in a simple and precise manner. This patent describes a device for determining a deposited dose, comprising: a measurement probe, comprising a U-shaped optical probe defining two output ends, the optical probe comprising at least one active portion made of scintillating material and intended to emit scintillation photons under the effect of incident ionizing radiation and at least two transport portions, placed on either side of the active portion and configured to carry the scintillation photons emitted by the active portion to the two outputs; a detection system comprising at least two photodetectors, each photodetector being connected to a respective output end of the U-shaped optical probe to receive and count scintillation photons received from the output end; and a processing module, configured to determine the deposited dose from the measurements carried out by the photodetectors.

This solution is more effective than solutions using only a theoretical model and CT scan images and provides real information in the form of indicators corresponding to two specific dosimetric quantities, namely, the scanner dose index (CTDI) and the dose length product (DLP).

Patent application WO2012129661A1 proposes a planar and volumetric dosimeter to be used with a radiotherapy machine having a radiation source. The dosimeter comprises a scintillating assembly comprising a plurality of scintillating optical fibers and configured to generate a luminous flux in response to the dose distribution that is incident thereon from the radiation source, and a photodetector operable to convert the optical energy emitted by the scintillator assembly into electrical signals to determine the actual two-dimensional (2D) or three-dimensional (3D) dose distribution that is incident on the scintillator assembly using a tomographic reconstruction algorithm.

U.S. Pat. No. 8,714,818 describes another example of a medical imaging system comprising a radiation source, a radiation sensor, a data collection unit and an imaging system. The radiation source has an opening for directing a collimated radiation beam in a direction toward a patient. The radiation sensor is placed near the opening and within the collimated radiation beam to measure a fluence of the collimated radiation beam. The data collection unit is arranged to collect radiation from the collimated beam after interaction with the patient. The imaging system is in communication with the data collection unit and configured to generate an image of a portion of the patient from the collected radiation.

Drawbacks of the Prior Art

The solutions of the prior art are not completely satisfactory because they do not make it possible to construct truly reliable indicators with sufficient definition to determine the dose per body zone. However, the exact knowledge of the effective dose delivered at the pelvis, the thorax, the lungs, the skull, etc., and not only estimated by a simulation, is an important piece of data to adjust the operation of a scanner as well as possible, to build indicators corresponding to references by type of patient, by operator or by equipment, and to determine the temporal evolution of imaging practices, as well as to make comparisons between the doses delivered during a sequence and the reference doses recommended for a scanner sequence.

BRIEF SUMMARY

In order to remedy these drawbacks, the present disclosure relates, in its most general sense, to a method for processing data relating to a radiological examination of a patient by means of a determining device, comprising acquiring doses ($C_i$, $t_i$) measured at a plurality of times $t_i$, storing these time-stamped measurements of radiation doses, and acquiring a DICOM digital file, characterized in that it comprises the following steps:

acquiring and storing the DICOM digital file delivered by the tomograph or scanner (3) during a tomography;

acquiring and storing the time-stamped measurements of the doses detected via a scintillating fiber (5) placed on the table (2), and time-stamped movements of the table (2);

interpolating the measurements ($C_i$, $t_i$) with data of the image (DICOM) in a common interpolated space and constructing a table ($C_k$, $DICOM_k$) in the interpolated space; and determining a table of the average dose levels $T_z$ in each slice T depending on the data ($DICOM_k$, $C_k$).

Preferably, the method further comprises a step of determining a corrective factor for compensating the measurement consistency.

Advantageously, the method further comprises a step of determining a corrective factor for compensating the energy dependence effects.

Preferably, the corrective factor is determined as a function of the difference between the clinical beam and the beam used for calibrating the dosimeter.

According to a variant, the corrective factor is determined by processing consisting in initially defining the difference between the average energy of the clinical X-ray beam and the average energy of the reference beam used during calibration by measuring the half-value layer (HVL) of the clinical beam, then applying the correction of the corresponding calibration factor.

BRIEF DESCRIPTION OF THE DRAWINGS

Embodiments of the present disclosure will be better understood on reading the following description, which concerns non-limiting embodiments illustrated by the appended drawings, in which:

FIG. 1 shows a schematic view of the data processing model according to the present disclosure;

FIG. 2 shows the functional diagram of the method that is the subject of the present disclosure; and FIG. 3 shows the succession of the processing operations that are the subject of the present disclosure.

DETAILED DESCRIPTION

FIG. 1 shows a schematic view of the operation of a digital tomographic scanner (3). A rotating frame supporting an X-ray source as well as the detector or a detector array moves according to a rotary movement around the patient (1). The latter is immobilized on a table (2) moving along an axis Z parallel to the axis of rotation of the rotating frame. The combination of the translation of the table (2) and the rotation of the frame supporting the scanner (3) results in data acquisition according to a relative helical movement (4). A scintillating fiber (5), or a series of scintillating fibers, is secured to the table (2) and is placed under the patient. This fiber (5) is optically connected to a dosimeter (6), which comprises a photonic detector, integrated into a housing fastened to the table (2). This housing may further comprise an accelerometer to provide an integrable electrical signal to determine the movement and therefore the position of the table (2). The fiber (5) provides information on the real dose absorbed by the fiber, having a density close to that of water, so as not to disturb the measurement of the detectors of the CT scanner.

A computer (10), which may comprise a server, receives:

The technical data of the tomograph and, in particular, the signals coming from the detectors, and generally already in DICOM format, to store them in a database (11).

The data from the dosimeter (6) to store them in a database (13).

General digital information corresponding to the medical examination and the patient from additional equipment (30) (FIG. 2). This additional equipment allows the real-time display of the dose measurements carried out by the dosimeter (6), as well as the post-examination display of the processed dosimetric information (dose, dose indices, mapping, statistics, etc.).

This computer (10) can be organized into two computers (10, 20), each of which may comprise a server. In this case, the first computer processes the local data, concerning the scans carried out with the scanner (3) and the local dosimeter (6), and the processing of these raw data is carried out on a second computer (20) shared by several medical imaging sites each having their own local computer (10).

All of the data processing is carried out between step 2.*b* and step 3 (see FIG. 2) at the computers (10 and 20).

Data relating to the radiation exposure of the patient during radiological procedures is stored in the database (11) and communicated in DICOM format for tomographic information object definitions. The DICOM digital format provides for different digital sequences, which can be used to convey exposure information:

the DICOM header, the procedure step performed by the DICOM modality (MPPS), the DICOM radiation dose structured report (RDSR), and the patient radiation dose structured report (P-RDSR).

These three digital sequences contain equipment output information of the scanner (3) and provide the equipment output information as well as patient and scan procedure information.

The object of the present disclosure is to provide a solution for determining, as closely as possible to reality, the real dose to which a patient has been exposed, and more precisely to allow the determination of the real dose of the main areas of the human body, in particular areas that are particularly sensitive to radiation exposure such as the brain or the pelvic area, by neutralizing the artifacts resulting from the state of the equipment and the volume and nature of the tissues interposed between the dosimetric probe and the radiation source, the patient's bodily specificities, the typology of the scan sequence and the quality of the images to be produced: factors such as the lack of uniformity among the machines used to perform the scans, which not only vary between manufacturers but are also devices complex enough to have individual variations in uniformity, affect dosimetric measurements. The dose received by a patient also depends on how the tomograph is used and the configuration of the various parameters for a particular imaging session. The aging of the equipment also brings disturbances in the quality of the acquired data: the radiation source, for example, the X-ray tube, tends to degrade over time when the machine is used. To achieve similar image quality, a machine tends to have to operate at higher current (mA) as tube efficiency decreases.

It also aims to correct the measurement errors of the dosimeter alone, collecting a real dose of radiation during the scan sequence, but with an approximate model and aberrations due to the positioning of the fiber under the patient, which introduces partial non-modelable masking of the radiation measured by the scintillating fiber.

This objective is achieved by embodiments of the present disclosure by combining three information sources of different natures, and which have different temporalities:

irradiation files from the dosimeter (6), received by the computer (10) in the form of raw signals sampled over time: a numeric dose value every millisecond throughout the examination;

DICOM images, comprising metadata (DICOM tags) from the scanner (3); and a report formatted by the computer (10), resulting from the dose report and/or from the DICOM SR, also provided by the scanner (3).

The present disclosure relates particularly to the nature of the processing applied to these data and, in particular, to their combinations to provide reliable indicators of effective doses, by area of the patient's body. The method consists in applying a succession of steps:

Step (100): acquiring and storing raw measurements;

Step (110): data preprocessing;

Step (120): using the data;

Step (200): mapping patient data;

Step (300): correcting raw measurements and calibrating;

Step (400): correcting the calibration factor;

Step (500): converting into CTDI and DLP dose indicators;

Step (600): time-space conversion;

Step (700): dose mapping; and

Step (800): using the data.

Step 100: Acquiring and Storing Raw Measurements

This step (100) relates to acquiring and storing the measurement data originating on the one hand from the dosimeter (6) and on the other hand from the DICOM files of the scanner (3) as well as spatial data (15). Spatial data can be provided by:

An accelerometer or any other telemetry device integrated into the dosimeter (6); AND/OR Scanner (3) DICOM files; AND/OR An independent telemetry device.

The data from the dosimeter (6) are the sampled radiation measurement signals detected by the scintillating fiber(s) (5). These data are timestamped by the dosimeter (6) or by the computer (10) controlling storing in the database (12).

These data also relate to the time-stamped position of the mobile table (2), obtained by a position sensor or by an accelerometer integrated into the dosimeter housing (6) or even by a position sensor integrated into the scanner (3). The combination of the irradiation and position measurement information makes it possible to calculate information on the doses detected by the scintillating fiber(s) (5) as a function of the position on the longitudinal axis of the patient (1).

The data from the scanner (3) are the DICOM file comprising the image of the patient colorized as a function of the signals provided by the detectors of the scanner, the dose structured report (RDSR type) and the CTDI measurement in microgray, for example, as a function of the transverse position, for a given longitudinal position.

Steps (110 and 120): Data Preprocessing and Use

These data are pre-processed by the computer (10):

Precutting of the data measured by the dosimeter (6) to keep only the irradiation sequences; and Precutting of DICOM data from the scanner (3) into different sequences to match measurements.

The computer (10) transmits the preprocessed measured data to the user interface of the additional equipment (30) for real-time display of the measurement curves.

All recovered and preprocessed data are also transmitted to the second computer (20), which may be a server shared between several scanners for specific processing.

Step (200): Mapping Patient Data

This step concerns matching the measurement sequences with the different clinical acquisitions (content of the corresponding DICOM files).

The measured data from the dosimeter (6) must be able to be associated with a patient examination in order to be able to automatically enter the measured dose in the patient file. To do this, an algorithmic model merging method ("mergence algorithm") is used, for example, according to processing based on Delaunay triangulation. This processing makes it possible to establish a link between the measurements carried out by the dosimeter and the information relating to the medical examination and the patient in order to associate the measured dose with the patient file:

the correspondence between the irradiation data from the dosimeter and the DICOM images on the one hand, and the correspondence between the DICOM images and the acquisitions referenced in the DICOM SR dose report on the other hand.

Establishing these correspondences makes it possible to calculate the CTDI (Computed Tomography Dose Index) dose indicators and the estimated tissue risk factor (PDL) specific to each patient, and to compare them with the values indicated by the scanner in the dose report and/or DICOM SR.

The difficulty of data merging comes from the variety of examinations and associated clinical protocols. For example, the correspondence between the irradiations and the DICOM images can be established in two stages:

The first step consists in determining which images and which irradiation sequences will be used to establish the mergence (certain images and sequences not corresponding to a patient examination, for example).

The second step consists in matching the acquisition times (from DICOM images) and irradiation times (from measurements taken by the dosimeter) using an error minimization approach similar to the least squares method in order to match each shot to an image and dose.

The raw measurement, associated with a shot or a series of shots (or irradiation) carried out by the scanner, can then be converted into a dose (in Gy or in Sv) by applying a calibration factor.

Indeed, the irradiation data from the dosimeter are raw, uncalibrated data. The scintillating optical fiber, when placed in the irradiation field (direct or diffused radiation), will capture and transform the energy delivered by the radiation from the X-ray tube into light photons according to a scintillation process. A quantity of light is then measured, by photon counting method, that is proportional to the dose deposited in the probe.

Thus, to transform the measured light into a dose (in the chosen unit), in particular, into Kerma in the air, Dose in the water at the surface, dose in the water at depth, effective dose, etc., a series of processing operations is applied.

Step (300): Calibration and Corrective Factors to be Applied to the Dose Measurement This step (300) consists in applying a calibration factor N, which makes it possible to link the measurements of the dosimeter (6) to a national reference. The dosimeter is calibrated by a calibration laboratory for one or more beam qualities and in a unit that may be the air kerma in RQT9 beam quality (reference in the field of scanners). In this case, the corresponding calibration factor is denoted $N_{k(RQT9)}$.

This step (300) also comprises compensating for certain sources of variability. Thus, a first processing relates to improving the spatial uniformity of response of the detector and a second processing relates to taking into account the energy dependence of the detector.

Step (310): Measurement Uniformity Compensation

Due to the characteristics, the use of scintillating fiber for radiation detection allows use in many hitherto inaccessible fields because the other technologies have characteristics that are not compatible with these fields. For example, an ionization chamber or a semiconductor detector cannot be used as an imaging dosimeter in routine clinical practice because this would disturb the images, these detectors not being radiolucent, unlike a scintillating plastic fiber.

Furthermore, the small size of a scintillating fiber makes it invisible and does not cause any discomfort for the patient, which is not the case with other real-time measurement technologies.

In order to satisfy the regulations concerning dosimeters dedicated to radiodiagnostics (IEC61674), the loss must be less than 3% all along the active detection part. This is not the case if no correction is made, even if the probes are made according to a very strict protocol. Furthermore, the production of such probes, with so many constraints in terms of their manufacture, cannot be envisaged at the industrial level because they would be far too expensive.

The natural response variations of the scintillating fiber along its axis must therefore be compensated for in order to guarantee a uniformity of response over the whole of the "assigned length" of the probe. The compensation is based on the application of a compensation model defined from measurements taken for each dosimeter when it is installed on a scanner. For example, this model implements the following steps:

Evaluating the average response, denoted R, of the probe over its entire length owing to progressive and continuous longitudinal irradiation of the scintillating fiber placed on the scanner table such that:

$$\overline{R} = \frac{\int_0^{L_{probe}} (I_1 + I_2)dz}{L_{probe}} \qquad \text{[Equation 1]}$$

where $L_{probe}$ corresponds to the length of the scintillating fiber and $I_1$ and $I_2$ the light measurements at both ends of the probe.

Evaluating the relative scatter between the quantities of light measured at the output of the two optical channels $I_1$ and $I_2$. The relative scatter, for each sample i being of the form:

$$E_r(i) = \frac{I_1(i) - I_2(i)}{I_1(i) + I_2(i)} \qquad \text{[Equation 2]}$$

Evaluating the deviation from the mean response ε

$$\varepsilon(i) = \frac{I_1(i) + I_2(i) - \bar{R}}{\bar{R}}$$

i corresponds either to a temporal coordinate or to a spatial coordinate

Evaluating the measurement error as a function of the irradiation position from the following quadratic linear regression:

$$\varepsilon = a \times E_r^2 + b \times E_r + c \quad \text{[Equation 3]}$$

Law obtained making it possible to compensate for the measurement error for each irradiation position on the scintillating fiber.

Step (320): Energy Dependence Compensation

The dosimeter (6) provides a dose measurement that may have an energy dependence depending on the dose unit in question: a scanner can irradiate with several different "beam qualities," and of different average energies, depending on the clinical examination to be performed. Because of this, the measurement error can reach +/−30%. An energy dependence correction algorithm serves to correct this situation.

The application of this correction therefore requires knowledge of the "beam quality" (i.e., of the average energy of the beam) for each irradiation. Since this information is not provided by the scanner, we have implemented a series of calibration measurements each time a dosimeter a scanner is installed, in order to determine all the qualities of the beams available for each scanner and for each type of irradiation.

Half-value layer (HVL) measurement is an example of a method for determining beam quality.

It is also possible to determine the "beam quality" corresponding to an examination, for example, by comparing dosimeters that do not have the same detection material (for example, an ionization chamber for which the detection medium is air and our dosimeter for which the detection medium is plastic).

Knowing the beam quality then makes it possible to define a deviation ΔE between the average energy of the beam and the average energy of the beam used during the calibration of the dosimeter.

The response curve of the dosimeter (characterization curve in different beam qualities obtained owing to measurements carried out in the laboratory with a device representative of the dosimeter (6) and an ionization chamber dosimeter used as a reference) then makes it possible to apply the correction to the calibration factor.

Step (400): Calibration Factor Correction

Thus, considering that the device was calibrated in air kerma in the RQT9 beam quality, we obtain:

$$Nk_{corrected} = Nk_{RQT9} \times Nk^* \quad \text{[Equation 4]}$$

where Nk* corresponds to the energy dependence correction factor defined by the difference between the scanner beam quality and the RQT9 beam quality used to calibrate the device.

After step (400), a dose (or dose rate) measurement is obtained in the desired unit (Gy or Sv depending on the "type" of dose: air kerma, water dose, etc.).

In the field of CT scans, the dosimetric indicators that must be entered in the patient file are the CTDI (computed tomography dose index) and the DLP (Dose Length Product).

In order to deliver this information, it is then necessary to convert the dose measurement (i.e., to transform the measured dose rate curve into a CTDI and DLP equivalent).

Step (500): Transformation of the Measured Dose into a Dose Indicator Dedicated to CT Scans The computer (10) also controls processing to calculate the CTDI and the DLP for each patient, for each irradiation or each series of irradiations and for the whole of a patient examination (i.e., sum of all irradiations for the same examination).

By applying corrective factors, this processing takes into account the cases where the patient is not perfectly positioned on the bed, which can induce a non-negligible bias at the conversion factor. It consists in applying one or more dose index conversion factors (CTDI, DLP, effective dose, organ dose, etc.).

The processing makes it possible to define an instantaneous CTDI(i) for each sample i corresponding to a measurement point. The value of this improvement lies in better taking into account, in particular, the dose modulation effect of the scanners and more precisely measuring the dose deposited at the at-risk organs (i.e., the dose modulation algorithms of the scanners are applied, in particular, to reduce the dose when the scanner passes over a sensitive organ (lungs, lens, etc.).

It is generally represented by:

$$CTDI_{FMX}(i) = \frac{N_C \times \text{Collimation}}{1000 \times \text{TableFeedPerRotation}} \sum_{j=-\frac{P}{2}}^{\frac{P}{2}} \dot{K}a(i+j) \quad \text{[Equation 5]}$$

where:
P is the number of samples for one revolution;
$N_C$ is a conversion factor making it possible to convert the dose measured in the fiber to the average dose in a slice of the irradiated volume;
$\dot{K}a(i)$ is the sample i of the instantaneous air kerma flow measurement (mGy·s$^{-1}$);
N is the total number of samples of the acquisition;
Collimation is the total collimation used for the shot (cm);
TableFeedPerRotation is the displacement of the table during the duration of one revolution (cm);
The factor $\frac{1}{1000}$ corresponds to 1 ms (s); and
collimation/TableFeedPerRotation=1 if the acquisition is not a helix.

The algorithms giving the average CTDI of the irradiation, the DLP and the cumulative dose indicators per examination are described in the document cited above.

Once these dose indicators are defined, we can compare them to the values displayed by the scanner and assess the deviation.

These deviations are calculated both for the CTDIs of the examination and for the CTDIs of the different shots. This formula is also valid for defining DLP deviations.

Step (600): Determining the Position of an Irradiation and Dose Mapping

This step concerns the correlation between the corrected, calibrated and converted data M(t) and the positions p at time t=>M(p).

Having two measurement channels, at each end of the detection probe, makes it possible to define the irradiation position. This is known from the literature and is, in particular, described in U.S. Pat. No. 5,704,890 (Page 9—Determination of location by pulse height).

Since this method is deemed to be unreliable with an unsatisfactory spatial resolution, in particular, taking into account the "pollution" of the signal (= of the dose) being measured due to the radiation scattered and backscattered by the patient, we used this technique only to define the direction of irradiation (movement of the bed).

Combining this technique with an analysis of the DICOM images from the scanner and/or any element making it possible to measure a position at each time t makes it possible to carry out a time-space conversion, i.e., to convert the measured irradiation times into irradiation positions (for each time t for which a dose is measured, a position i is calculated).

This makes it possible to obtain a dose and/or local CTDI value for each irradiation position and to cumulate all the irradiations of the same examination if necessary.

In order to have a more meaningful and more relevant visual rendering, once this first conversion has been carried out, we proceed to the passage in the spatial reference of the patient, that is to say, we make each position defined above correspond to a pixel of an image of the patient (this image can correspond, for example, to a locate, also called topogram or scout).

By way of example, an element making it possible to measure a position at each time t can be an accelerometer. It allows the position to be determined more precisely and can enrich the method using only an analysis of the DICOM images of the scanner. The advantage of its use in addition to the analysis of DICOM images is that if the image is not available, it will still be possible to associate a position with each irradiation time and therefore proceed with the accumulation if there are several intersecting irradiations.

Step (700): Dose Mapping

Step (600) described above makes it possible to obtain a dose/dose rate and/or CTDI(i) value for each irradiation position. The processing, in particular, performs the colorization of the patient images as a function of the dose measurements calculated for each position p.

Step (800): Use on the Computer (10)

The computing center (second computer 20) sends the processed data to the computer (10), which saves the results locally and uses the data to display the results on a graphical interface.

The invention claimed is:

1. A method for processing data relating to a radiological examination of a patient by way of a determining device, the method comprising:

acquiring doses ($C_i$, $t_i$) measured at a plurality of times $t_i$, and storing these time-stamped measurements of radiation doses;

acquiring and storing at least one DICOM digital file delivered by a tomograph during or after a tomography, the DICOM digital file containing information on the radiological examination including DICOM images of the patient;

acquiring and storing the time-stamped measurements of the radiation doses detected via a scintillating fiber placed on a table, and time-stamped movements of the table;

interpolating the time-stamped measurements of the acquired doses ($C_i$, $t_i$) with data of the DICOM images of the patient in a common interpolated space and constructing a table ($C_k$, $DICOM_k$) in the common interpolated space; and determining a table of average dose levels $T_z$ in each slice T depending on the data ($DICOM_k$, $C_k$).

2. The method of claim 1, further comprising determining a corrective factor for compensating measurement consistency.

3. The method of claim 1, further comprising determining a corrective factor for compensating energy dependence effects.

4. The method of claim 3, wherein the corrective factor is determined as a function of a difference between a clinical beam and a reference beam used for calibrating a dosimeter providing the time-stamped measurements of the radiation doses detected via the scintillating fiber.

5. The method of claim 4, wherein the corrective factor is determined by processing that includes initially defining the difference between an average energy of the clinical beam and an average energy of the reference beam used during calibration by measuring a half-value layer (HVL) of the clinical beam, then applying a correction of the corresponding calibration factor.

6. The method of claim 5, further comprising calculating an irradiation position p for each time t for which an irradiation dose is measured, and mapping, for each irradiation position p, a dose value by coloring the patient images as a function of the dose measurements.

* * * * *